United States Patent [19]

Gerhart et al.

[11] 4,423,073

[45] Dec. 27, 1983

[54] FLUORINATED DIAMINOPENTENE DERIVATIVES

[75] Inventors: Fritz Gerhart, Kehl-Leutesheim, Fed. Rep. of Germany; Viviane Van Dorsselaer, Strasbourg, France

[73] Assignee: Merrell Toraude et Compagnie, Strasbourg, France

[21] Appl. No.: 407,226

[22] Filed: Aug. 11, 1982

[30] Foreign Application Priority Data

Aug. 19, 1981 [GB] United Kingdom ............... 8125360

[51] Int. Cl.³ .................. C07C 101/28; C07C 87/26; A61K 31/13; A61K 31/22; A61K 31/195
[52] U.S. Cl. .................... 424/314; 424/319; 424/325; 560/169; 562/561; 564/509
[58] Field of Search .................. 424/314, 319, 325; 560/169; 562/561; 564/509

[56] References Cited

U.S. PATENT DOCUMENTS 4,323,704 4/1982 Metcalf et al. .................. 562/561

FOREIGN PATENT DOCUMENTS 2001960 2/1979 United Kingdom .
2003876 3/1979 United Kingdom .
2104072 3/1983 United Kingdom .

*Primary Examiner*—Natalie Trousof
*Assistant Examiner*—Patricia M. Scott
*Attorney, Agent, or Firm*—Gary D. Street; Raymond A. McDonald

[57] ABSTRACT

Novel fluorinated alkenylene diamine derivatives are inhibitors of ornithine decarboxylase enzyme and have the following general Formula I:

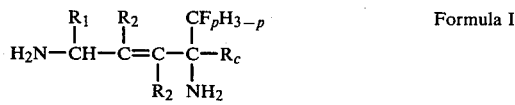

Formula I wherein:
$R_c$ represents hydrogen or —COR$_5$, where R$_5$ is as defined below;
$R_1$ represents hydrogen or C$_1$-C$_6$ alkyl;
one of R$_2$ and R$_3$ represents hydrogen and the other represents C$_1$-C$_6$ alkyl.
$R_5$ represents hydroxy or C$_1$-C$_8$ alkoxy; and
p represents 1 or 2.

17 Claims, No Drawings

FLUORINATED DIAMINOPENTENE DERIVATIVES

FIELD OF THE INVENTION

The invention relates to novel pharmaceutically useful fluorinated alkenylene diamine derivatives which in vivo are inhibitors of a decarboxylase enzyme involved in polyamine formation in organisms. The invention provides the compounds per se, pharmaceutical compositions comprising said compounds, methods of medical treatment using said compounds, and processes for preparing said compounds.

BACKGROUND OF THE INVENTION

The decarboxylation of ornithine to putrescine, a reaction catalyzed by the enzyme ornithine decarboxylase (ODC), is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-Adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in embryonic tissue; in the testes, ventral prostrate, and thymus; in tumor tissue; in psoriatic skin lesions; and in other cells undergoing rapid growth or proliferation.

Since putrescine is the precursor of both spermidine and spermine, blockade of the conversion of ornithine to putrescine, such as by inhibition of ODC, should prevent new biosynthesis of these polyamines and, thus, provide beneficial physiological effects.

We have disclosed in U.K. Patent Specification No. 2001960A that inter alia compounds of the following Formula A are inhibitors of ornithine decarboxylase:

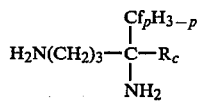

Formula A wherein:
$R_c$ represents —$COR_5$, where $R_5$ represents hydroxy or $C_1$–$C_8$ alkoxy; and
p represents 1 or 2.

Further, we have disclosed in U.K. Patent Specification No. 2003876 that the analogues of said compounds of Formula A in which $R_c$ represents hydrogen are likewise ornithine decarboxylase inhibitors.

SUMMARY OF THE INVENTION

The compounds of the invention are represented by the following general Formula I:

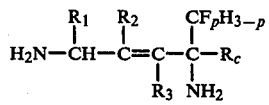

Formula I wherein:
$R_c$ represents hydrogen or —$COR_5$, where $R_5$ is as defined below;
$R_1$ represents hydrogen or $C_1$–$C_6$ alkyl;
one of $R_2$ and $R_3$ represents hydrogen and the other represents $C_1$–$C_6$ alkyl
$R_5$ represents hydroxy or $C_1$–$C_8$ alkoxy;
p represents 1 or 2.

Pharmaceutically acceptable salts and individual optical isomers of the compounds of general Formula I are also within the scope of the invention.

It is believed that the compounds of general Formula I are "substrate-induced irreversible inhibitors" of ornithine decarboxylase. Such inhibitors are also known in the art as "enzyme-activated irreversible inhibitors", "suicide enzyme inhibitors", "$K_{cat}$ inhibitors", or "mechanism-based inhibitors". In order for a compound to be a substrate-induced irreversible enzyme inhibitor, the compound must be a substrate for the target enzyme, and the compound must contain a latent reactive group susceptible to being unmasked as the result of the normal catalytic action of the enzyme. The unmasking of the latent reactive group by the action of the enzyme generates a reactive function which alkylates a nucleophilic residue present at the active site of the enzyme. Thus, there is formed a covalent bond between the inhibitor and the enzyme at the active site resulting in irreversible inactivation of the enzyme. Such inhibitors are extremely specific since the inhibitor must be a substrate for the target enzyme and since biotransformation of the inhibitor by the target enzyme is required before the enzyme is inactivated. Although it is believed that the compounds of general Formula I generally exert their action by means of a substrate-induced mechanism, inhibition may occur by other mechanisms, such as by competitive inhibition.

The compounds of Formula I inhibit ornithine decarboxylase enzyme (ODC) in vivo, and produce a decrease in putrescine and spermidine concentrations in cells in which active biosynthesis is taking place. The compounds of Formula I, therefore, are useful in mammals for controlling undesirable cell growth or proliferation. The compounds of Formula I are useful pharmacological agents for treating those diseases or conditions that are known in the art to be characterized by high ODC activity. In particular, the compounds are useful systemically for controlling the growth of tumor tissues in laboratory animals for treating benign prostatic hypertrophy, and for controlling the growth of pathogenic parasitic protozoa in infected domestic animals and humans.

The compounds of Formula I can also be employed to study the presence and physiological function of ODC inhibition in biological systems and its relationship to pathological processes.

The compounds of Formula I wherein $R_c$ is an ester group do not inhibit ODC in vitro. In order to produce inhibition of ODC in vivo, said compounds must undergo biotransformation to the compounds of Formula I wherein $R_c$ is hydrogen or carboxy, which compounds are inhibitors of ODC both in vitro and in vivo.

It will be recognised that the compounds of Formula I can be substituted at the carboxyl group, if present, and/or amino group with any group known in the art to be capable of cleavage in vivo (enzymatically or chemically) to generate a free carboxylic and/or amino group. Compounds which contain such cleavable substituents and which, therefore, can be converted in vivo into a compound of Formula I will be equivalent to the compounds of Formula I for the purpose of this invention. Such derivatives can be prepared in manner known per se from the compounds of Formula I. A presently preferred derivative is N-glutamyl. The ODC activity of the compounds can be determined in vitro by the method described by B. Metcalf et al. *J. Am. Chem. Soc.*, 100, 2551 (1978). The ODC activity of the compounds of Formula I can be determined in vivo by the method of C. Danzin, *Biochemical Pharmacology*, 28, 627 (1979).

DETAILED DESCRIPTION OF THE INVENTION

In the above general Formula I, $R_c$ represents hydrogen, carboxy (i.e. $R_5$ is hydroxy) or alkoxycarbonyl (i.e. $R_5$ is $C_1$-$C_8$ alkoxy).

In the above general Formula I, $R_1$, $R_2$ and $R_3$ independently represent hydrogen or $C_1$-$C_6$ alkyl, especially methyl except that one of $R_2$ and $R_3$ must be hydrogen and the other of $R_2$ and $R_3$ must be alkyl. Preferably $R_1$ is hydrogen and it is further preferred that $R_3$ is hydrogen.

References in this Specification, including the Claims, to an alkyl group or moiety mean a straight or branched chain alkyl group or moiety and, in the case of an alkyl group or moiety having structural isomers, includes all of those isomers and mixtures thereof unless a particular isomer is specified or clearly implied by the context.

Illustrative examples of straight or branched chain alkyl groups or moieties having 1 to 4 carbon atoms are methyl, ethyl, n-propyl, iso-propyl and n-butyl.

Illustrative examples of straight or branched chain alkyl groups of moieties having 1 to 6 carbon atoms are those specified above having 1 to 4 carbon atoms and n-pentyl, neo-pentyl, n-hexyl and iso-hexyl.

Illustrative examples of straight or branched chain alkyl groups or moieties having 1 to 8 carbon atoms are those specified above having 1 to 6 carbon atoms and n-heptyl, 5-methylhexyl and n-octyl.

It will be appreciated that the compounds of the invention specified in Table I below are the alkyl-substituted fluorinated methyl dehydro analogues of the respective specified naturally occurring amino acid or diamine.

TABLE I

| Formula I | | | | |
|---|---|---|---|---|
| $R_1$ | $R_a$ | $R_b$ | $R_c$ | Analogue |
| H | H | H | $CO_2H$ | ornithine |
| H | H | H | H | putrescine |

In the above general Formula I, p represents 1 or 2. It will be appreciated that when p represents 1, the compounds of the invention are mono-fluoromethyl derivatives and that when p represents 2 they are difluoromethyl derivatives. It presently is preferred that p is 1.

As indicated in general Formula I, the compounds of the invention are in trans, or entgegen, configuration.

Trans isomers are indicated in the nomenclature used in this Specification, including the Claims, by the letter "E". The invention includes, of course, non-toxic mixtures of said isomer with its cis isomer.

Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as, organic carboxylic acids, for example salicyclic, maleic, malonic, tartaric, citric and ascorbic acids, and organic sulfonic acids, for example methane sulfonic acid; and non-toxic salts formed with inorganic or organic bases, such as, hydroxides of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, methylaminoethanol, ethanolamine and piperidine. The salts are prepared by conventional means.

In one embodiment of the invention, there are provided compounds of the following general Formula IA:

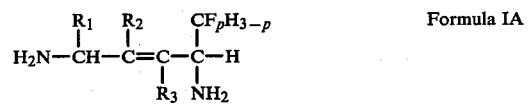

Formula IA wherein
$R_1$, $R_2$, $R_3$, and p are defined in connection with Formula I;
and pharmaceutically acceptable salts thereof.

In another embodiment of the invention, there are provided compounds of the following general Formula IB:

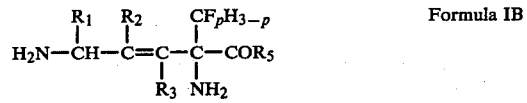

Formula IB wherein
$R_1$, $R_2$, $R_3$, $R_5$, and p are as defined in connection with Formula I;
and pharmaceutically acceptable salts thereof.

It is especially preferred that in Formulae IA and IB both $R_1$ and $R_3$ are hydrogen.

Illustrative examples of compounds of the present invention are the following:
1-fluoro-2,5-diamino-3-methyl-3-(E)-pentene;
1,1-difluoro-2,5-diamino-3-methyl-3-(E)-pentene;
2-fluoromethyl-2,5-diamino-3-methyl-3-(E)-penten-1-oic acid;
2-difluoromethyl-2,5-diamino-3-methyl-3-(E)-penten-1-oic acid;
ethyl 2-fluoromethyl-2,5-diamino-3-methyl-3-(E)-penten-1-oate;
ethyl 2-difluoromethyl-2,5-diamino-3-methyl-3-(E)-penten-1-oate;
1-fluoro-2,5-diamino-4-methyl-3(E)-pentene;
1,1-difluoro-2,5-diamino-4-methyl-3-(E)-pentene;
2-fluoromethyl-2,5-diamino-4-methyl-3-(E)-penten-1-oic acid;
2-difluoromethyl-2,5-diamino-4-methyl-3-(E)-penten-1-oic acid;

ethyl 2-fluoromethyl-2,5-diamino-4-methyl-3-(E)-penten-1-oate;
ethyl 2-difluoromethyl-2,5-diamino-4-methyl-3-(E)-penten-1-oate;
1-fluoro-2,5-diamino-3-ethyl-3-(E)-pentene;
1,1-difluoro-2,5-diamino-4-ethyl-3-(E)-pentene;
2-fluoromethyl-2,5-diamino-4-ethyl-3-(E)-penten-1-oic acid;
2-difluoromethyl-2,5-diamino-3-ethyl-3-(E)-penten-1-oic acid;
1-fluoro-2,5-diamino-4-propyl-3-(E)-pentene;
1,1-difluoro-2,5-diamino-3-hexyl-3-(E)-pentene;
2-fluoromethyl-2,5-diamino-4-hexyl-3-(E)-penten-1-oic acid;
2-difluoromethyl-2,5-diamino-3-butyl-3-(E)-penten-1-oic acid;
1-fluoro-2,5-diamino-4-methyl-3-(E)-hexene;
1,1-difluoro-2,5-diamino-3-methyl-3-(E)-hexene;
1-fluoro-2,5-diamino-4-methyl-3-(E)-heptene;
1,1-difluoro-2,5-diamino-4-methyl-3-(E)-heptene.

The effect of the compounds of Formula I for the control of the growth rate of rapidly proliferating tumor tissue can be assessed in standard animal tumor models after oral or parenteral administration. For example, the antitumor effects can be demonstrated in the following models: (a) L1210 leukemia in mice, (b) EMT 6 tumor in Balb/C mice, (c) 7,12-dimethylbenzanthracene-induced (DMBA-induced) mammary tumor in rats, or (d) Morris 7288 C or 5123 hepatoma in Buffalo rats. In addition, the antitumor effects of the compounds in combination with chemotherapeutic agents can be demonstrated in animal models.

The term "controlling the growth of pathogenic parasitic protozoa", as used herein, means slowing, interrupting, arresting, or stopping the replication of the protozoa in an infected host. The compounds of Formula I are particularly useful against $T.b.$ brucei (which causes trypanosomiasis in cattle), $T.b.$ rhodesiense, (which causes human sleeping sick-sickness), the coccidia, for example, Eimeria tenella (which causes intestinal coccidiosis in fowl (e.g. chickens, turkeys, and ducks)) and the exoerythrocytic form of plasmodia, for example, plasmodium falciparum (which causes human malaria).

The antiprotazoal activity of the compounds of Formula I can be demonstrated in vivo or in vitro in standard microbiological test procedures. For example, the activity of the compounds against $T.b.$ brucei, and $T.b.$ rhodesiense can be determined in infected mice by administering the test compound ad lib daily (3 to 15 days post infection) as a solution in the drinking water. Activity is indicated by an increase in survival time (as compared to untreated controls) or by the absence of parasites in the blood. The activity of the compounds against the coccidia can be determined in infected chickens, for example those infected with $E.$ tenella by determining the test compound daily ad lib (from one day pre injection to five days post infection) as a solution in the drinking water. The cecal lesions are evaluated by a standard lesion scoring procedure. (See Reid. Am. J. Vet. Res., 30, 447 (1969) and Avian Coccidiosis, P. Long. Editor, British Poultry Science, Ltd., Edinburgh). The activity of the compounds against malaria ($p.$ faleiparum) can be determined by a standard in vitro plate culture test (See K. Rieckmann et al, Lancet, 1, 22 (1978)). Antimalarial activity can also be determined in special strains of mice infected with the exoerythrocitic form of $p.$berghei. In this test, the compound is administered ad lib in drinking water starting two days preinfection and continuing 28 days postinfection. Activity is measured by a significant decrease in deaths as compared to controls or by a significant increase in survival time.

The compounds of Formula I wherein $R_c$ is —$COR_5$ are also capable of interrupting embryogenesis in female mammals when administered systematically. Thus, the compounds are useful as contragestational agents in female mammals when it is desired to terminate early pregnancy. The contragestational activity of the compounds can be demonstrated in mice by the method of J. Fozard, European Journal of Pharmacology, 65, 379 (1980). In general, an effective daily dose of the compounds of Formula I, wherein $R_c$ is —$COR_5$, for terminating pregnancy in warm-blooded mammals is from 10 mg/kg to 1 g/kg, preferably 10 to 100 mg/kg, administered after fertilisation during the period between Standard Stages 8–16 of gestation as defined by E. Wischi (See Tables 26–27, pages 82–92, Biology Data Book, Altman and Dittmer, Editors, Published by the Federation of American Societies for Experimental Biology, Washington, D.C., 1964). The period of treatment will vary with the species. In humans, the period of treatment will extend from the 6th–7th day of gestation to the 27th day.

The compounds of this invention can be administered in various manners to achieve the desired effect. The compounds can be administered alone or in the form of pharmaceutical preparations either orally or parenterally, for example, subcutaneously, intravenously or interperitoneally. The amount of novel compound administered will vary and can be any effective amount. Depending upon the patient, the condition being treated and the mode of administration, the effective dosage of the compound administered may vary from about 5 mg/kg to about 100 mg/kg, of body weight of the patient per day. Unit doses of these compounds can contain, for example, from about 10 mg of 300 mg of the compounds and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known per se in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

Methods of preparing the compounds of Formula I will now be described. If in any of the reaction steps described an amino group of a reactant would be involved in an unwanted reaction under the relevant reaction conditions, the amino group will be protected in manner known per se by introduction of an appropriate protecting group. The protecting group will be chosen having regard to the nature of the relevant reaction and ease of removal to free the amino group. The protecting group can be selected from, for example, acyl, for example, lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl and the like; carbobenzoxy, benzenesulfonyl and tosyl. Both amino hydrogen atoms can be substituted by a single protecting group such as, for example phthaloyl. The protecting groups are introduced in manner known per se by, for example, reaction of the amine with a lower alkanoyl or aroyl chloride, anhydride, sulfonylchloride, tert-butoxycarbonyl-oxyimino-2-phenyl-acetonitrile (BOC-ON), or di-tert-butyl dicarbonate ((BOC)$_2$O).

Removal of the protecting group after the required reaction has been completed can be carried out in manner known per se for the relevant protecting group. Usually, said removal will be by hydrolytic cleavage using a strong organic or mineral acid such as, for example, trifluoroacetic acid, hydrochloric acid and the like acids; or by hydrogen chloride gas under anhydrous conditions. The use of conditions which will react with the olefinic double bond or of reactants, such as hydrobromic acid, which will react with the olefinic double bond must be avoided. Solvents used will be chosen dependent upon the conditions of protecting group removal. For example, ethers such as, for example, diethylether can be used for cleavage using hydrogen chloride gas.

The compounds of Formula I can be prepared in manner known per se from the corresponding compound of the following general Formula II:

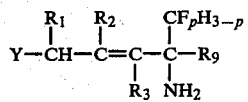

Formula II wherein:
R$_1$, R$_2$, R$_3$ and p are defined in connection with Formula I;
R$_9$ represents hydrogen, cyano or C$_2$–C$_9$ alkoxycarbonyl; and
Y represents a leaving group such as hydroxy bromine, chlorine, iodine, tosyloxy (i.e. toluene-p-solufonyl-oxy) or mesyloxy (i.e. methanesulfonyloxy).

The reaction can proceed via the corresponding phthalimido derivative, as described below.

The amino group in the compound of Formula II will be protected in manner known per se during the reaction by a suitable subsequently removable protecting group or groups. The protecting group preferably is phthaloyl. When proceeding via the phthalimido derivative when p is 1, it is necessary to use a protecting group which does not leave any hydrogen atom on the amino group in order to obtain the desired compound of Formula I. Usually, the protecting group will be selected so that it is removed during the final step in the conversion of the compound of Formula II into the corresponding compound of Formula I.

The amino-protected derivative of a compound of Formula II with an appropriate leaving group can be treated with an alkali metal phthalimide, especially sodium or potassium phthalimide, in a polar organic solvent, such as for example, dimethylformamide, dimethylsulfoxide or hexamethylphosphoric triamide, to form the corresponding phthalimido derivative. Any of the leaving groups Y exemplified above except hydroxy is appropriate for this reaction. Conveniently one to three equivalents of the phthalimide salt are used per equivalent of compound of Formula II at a temperature of 25° to 100° C. for a period of 0.5 to 3 hours.

When Y is hydroxy, the amino-protected derivative of a compound of Formula II can be converted into the phthalimido derivative by reaction with phthalimide in the presence of a trialkyl- or triaryl-phosphine and diethylazodicarboxylate in an anhydrous aprotic solvent. Usually 1 to 3 equivalents each of phthalimide, the phosphine and diethyldiazo-dicarboxylate will be used per equivalent of alcohol reactant at a temperature of 10° C. to 100° C. for a period of 18 to 24 hours.

When R$_9$ is hydrogen or alkoxycarbonyl, the phthalimido derivative can be converted into the required compound of Formula I by heating with a reactant such as hydrazine or methylamine in a polar organic solvent such as, for example, an alkanol, preferably ethanol. Preferably hydrazine hydrate is used in an amount of about 2 equivalents per equivalent of phthalimido derivative. Suitably, the conversion is performed at 50° to 100° C., preferably under reflux conditions, for a period of 3 to 24 hours.

The phthalimido derivative of Formula II also can be converted into the required compound of Formula I by heating with a strong mineral acid such as hydrochloric acid or sulfuric acid. Said heating also hydrolyses any cyano group represented by R$_9$ to a carboxy group. Preferably a mixture of hydrochloric and acetic acid is used at a temperature of about 95° C. for about 24 hours. Acids, such as hydrobromic acid, which are reactive towards olefinic double bonds cannot be used.

Compounds of Formula II above in which R$_1$ is hydrogen and Y is bromine or iodine suitably can be obtained by boron tribromide or trialkysilyliodide cleavage in manner known per se of an allylic compound of the following general Formula III:

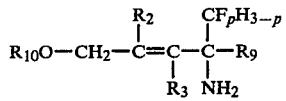

Formula III wherein:
R$_2$, R$_3$, R$_9$ and p are as defined in connection with Formula II; and
R$_{10}$ represents C$_1$–C$_4$ alkyl, preferably methyl.

Compounds of Formula II in which R$_1$ is hydrogen and Y is hydroxy also can be obtained from the corresponding compounds of Formula II in which Y is halogen by treatment with sodium acetate and acetic acid and subsequent reduction with, for example lithium aluminumium hydride, of the resultant acetate. When a compound of Formula II in which $R_1$ is $C_1$-$C_6$ alkyl and Y is hydroxy is required, a compound of Formula II obtained by said reduction is oxidized with, for example, dimethysulfoxide in the presence of oxalyl chloride and triethylamine at about $-78°$ C. and the resultant aldehyde reacted with, for example, the appropriate alkyl lithium.

Compounds of Formula III in which $R_9$ represents cyano can be obtained from the corresponding compounds of the following general Formula IV by treatment with an alkali metal or ammonium cyanide, such as, for example, sodium cyanide in water in the presence of a water soluble ammonium salt of a strong acid, especially ammonium chloride.

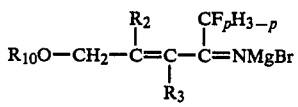   Formula IV wherein:
$R_2$, $R_3$, $R_{10}$ and p are as defined in connection with Formula III, Compounds of Formul III in which $R_9$ represents hydrogen, can be obtained from the corresponding compound of Formula IV by reduction with a reducing agent, such as a borohydride, which selectively reduces the imino group.

Compounds of Formula III in which $R_9$ represents alkoxycarbonyl can be obtained by hydrolysis of the corresponding compound of Formula III in which $R_9$ represents cyano in the presence of an acid, such as hydrochloric acid, and the corresponding alcohol.

Compounds of Formula IV can be obtained by treatment of the corresponding Grignard reactant of the following general Formula V with the corresponding fluorinated acetonitrile of the following general Formula VI:

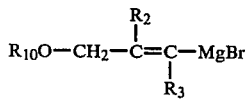   Formula V wherein $R_2$, $R_3$, and $R_{10}$ are as defined in connection with Formula IV;

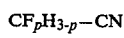   Formula VI wherein p represents 1 or 2.

The Grignard reactants of Formula V can be prepared in manner known per se from, for example, the corresponding bromides of the following general Formula VII and magnesium turnings in an appropriate solvent for Grignard type reactions.

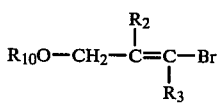   Formula VII wherein $R_2$, $R_3$ and $R_{10}$ are defined in connection with Formula V.

The bromides of Formula VII are known or can be prepared by analogous processes for obtaining said known compounds.

In the particular case of compounds of Formula II in which $R_1$ is hydrogen, $R_2$ is methyl and $R_9$ is hydrogen, the compounds of said formula can be prepared by allylic halogenation of a compound of the following Formula VIII.

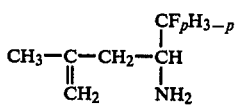   Formula VIII wherein p is 1 or 2 Conveniently, the halogenation can be carried out by the Wohl-Zeigler Reaction in which the compound of Formula III is treated with an N-haloamide, preferably an N-bromosuccinimide, usually in the presence of a free-radical initiator such as a peroxide or labile azo compound and under light irradiation.

The allylic halogenation of the compound of Formula VIII yields of mixture of the said compound of Formula II and the structural isomer of the following general Formula B:

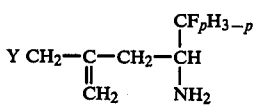   Formula B wherein:
Y represents halogen; and
p is 1 or 2.

These compounds can be separated in manner known per se but usually the mixture will be converted via the corresponding phthalimido derivature into a mixture of the corresponding diamines, which can then be separated by column chromatography of their di-BOC derivatives in the manner described below in connection with separation of acids of Formula I and Formula C.

Compounds of Formula VIII can be obtained by reducing with, for example, a borohydride the cyano compound obtained by treatment of a compound of the following Formula IX with an alkali metal or ammonium cyanide, such as, for example, sodium cyanide in water in the presence of a water soluble ammonium salt of a strong acid, especially ammonium chloride.

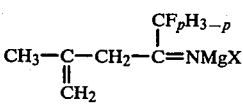   Formula IX wherein
p is 1 or 2 and;
X represents bromine, chlorine or iodine Compounds of Formula IX can be obtained by treatment of the corresponding Grignard reactant of the following general Formula X with the corresponding fluorinated acetonitrile of the following general Formula XI:

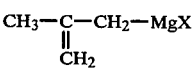   Formula X wherein X is as defined in connection with Formula IV;

$$CF_pH_{3-p}-CN \qquad \text{Formula XI}$$

wherein p is 1 or 2.

The Grignard reactants of Formula X can be prepared in manner known per se from, for example, the corresponding halides and magnesium turnings.

Compounds of Formula I in which $R_2$ is methyl and $R_c$ is carboxy also can be obtained by acid hydrolysis of an phthalimido compound of the following Formula XII.

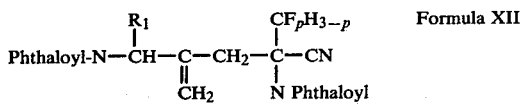

wherein
$R_1$ and p are as defined in connection with Formula I.

Said hydrolysis yields a mixture of the said compound of Formula I with a compound of the following Formula C:

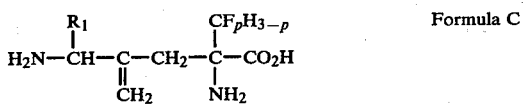

wherein:
$R_1$ and p are as define in connection with Formula I.
The said mixture compounds of Formula I and Formula C can be separated in manner known per se after derivatisation of the amino and carboxylic functions, for example first protecting both amino groups by treatment with tert-butoxycarbonyl- oxyimino-2-phenyl-acetonitrile (BOC-ON) and then forming the methyl ester by treatment with diazomethane, and separation of the di-BOC methyl esters in manner known per se by column chromatography. Subsequently, the separated derivatives can be treated in manner known per se to free the amino groups and/or the carboxy group. In connection with the derivatisation, it has been found that if the ester is formed without first protecting the amino groups, a cyclic product is obtained.

It will be appreciated that the order of some of the reaction steps in the process routes described above can be changed.

The esters of Formula I wherein $R_c$ is alkoxycarbonyl can be obtained in manner known per se from the corresponding acids of Formula I wherein $R_c$ is carboxy by esterification with the corresponding alcohol or by conversion of the terminal-amine protected acid into the corresponding acid chloride and alcoholysis of said acid chloride with the corresponding alcohol.

When necessary in the preparation of compounds of Formula I separation of cis/trans isomers or intermediates or final products can be carried out by chromatographic techniques.

The compunds of Formula I contain at least one asymmetrical carbon atom and therefore exists as stereoisomers. Methods of separating the steroisomers of a particular compound will be apparent to those skilled in the art. For example, when $R_1$ is hydrogen, the individual optical isomers of the compounds of Formula I may be separated in manner known per se using optically active acids or bases. In particular, the amino group distal to the fluorinated methyl group can be protected using a ($C_2$-$C_5$ alkoxycarbonyl) phthalimide in a solvent such as, for example tetrahydrofuran, diethyl ether or $C_1$-$C_4$ alkanol, e.g. as methanol or ethanol. The protected amine derivative is then resolved using a chiral acid. The resolved phthalimido compound is then deprotected using, for example, hydrazine or methylamine to remove the phthalimide group followed if required by acid or base hydrolysis to cleave the ester product to obtain the corresponding acid. The thus resolved acids, esters and amines may be employed to prepare the individual isomers of other compounds of the invention in the manner described hereinabove.

The compounds produced by the foregoing processes may be isolated either per se or as acid addition salts thereof.

The acid addition salts are preferably the pharmaceutically acceptable, non-toxic addition salts with suitable acids such as those previously referred to in this Specification. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable, acid additions salts, or are useful for identification or characterisation of the bases.

A resulting acid addition salt may be converted into the free compound according to known methods, for example, by treating it with an alkali or aklaline earth metal hydroxide or alkoxide; with an alkali metal or an alkaline earth metal carbonate or hydrogen carbonate; with trialkylamine; or with an anion exchange resin.

A resulting acid accition salt may also be converted into another acid addition salt according to known methods; for example, a salt with a inorganic acid may be treated with a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated by the following non-limiting Examples. All NMR measurements are given on the delta scale (i.e. tetramethylsilane=0).

EXAMPLE 1

Preparation of 1-fluoro-2,5-diamino-4-methyl-3-(E)-pentene, dihydrochloride (A) 1-Fluoro-2-amino-4-methyl-4-pentene

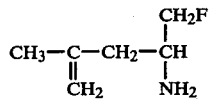

Under an atmosphere of nitrogen, methallyl-magnesium chloride is prepared from 97.2 g (4 moles) of magnesium turnings, methallyl chloride (90.6 g, 1 mole) and dry tetrahydrofuran (900 mL). The Grignard solution is separated from the excess of magnesium, cooled to −40° C. and fluoroacetonitrile (56 g, 950 mmoles) in dry tetrahydrofuran (200 mL) is added, dropwise, during about 1 hour. The reaction mixture is kept at −40° C. for an additional 30 minutes, and then poured into a stirred mixture of methanol (2 L), water (50 mL) and sodium borohydride (39 g) cooled at −40° C. After stirring for 1 hour at −30° C., the temperature is allowed to rise to 0° C. during 1 hour. After acidification with 6 N hydrochloric acid (about 500 mL) and evaporation, the residue is dissolved in water (about 2 L), and the solution is extracted 3 times with ether to remove non-basic by- products. The solution is made alkaline with 6 N sodium hodroxide and extracted 3 times with diethyl ether. The organic layer is dried over sodium sulfate and evaporation of the solvent affords 52.5 g of a colored oil (45 %).

NMR (CDCl): 1.67 (2H, s, —NH₂), 1.77 (3H, s), 2.10 (2H, m), 3.30 (1H, m), 4.33 (2H,d of m, $J_{H\text{-}F}=48$ Hz), 4.87 (2H, m).

(B) 1-Fluoro-2-phthalimido-4-methyl-4 pentene

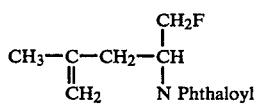

A mixture of 1-fluoro-2-amino-4-methyl-4-pentene (52.5 g, 450 mmoles) prepared as in step A above, N-carbethoxyphthalimide (98.55 g, 450 mmoles), and benzene (600 mL) is kept overnight at room temperature. The solution is concentrated under vacuum, the oily residue is dissolved in methylene chloride (500 mL) and treated with 50 g of triethylamine during 4 hours at room temperature. After extraction with 2 N hydrochloric acid (6×500 mL), the organic layer is dried over sodium sulfate and discoloured by filtration through a layer of silica gel and another of carbon black. The oily residue obtained after concentration (110 g) is extracted several times with petroleum ether to remove some insoluble N-carbethoxyphthalimide. Evaporation of the petroleum ether affords a yellow oil (94 g) which is crystallized from pentane at low temperature (85 g, 77%).

NMR (CDCl₃): 1.77 (3H, s), 2.65 (2H, m), 3.88-5.55 (3H, complex m), 4.70 (2H, broad s), 7.72 (4H, m).

(C) 1-Fluoro-2-phthalimido-4-methylene-5-bromopentane

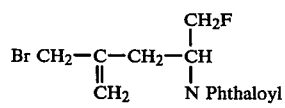

A mixture of 1-fluoro-2-phthalimido-4-methyl-4-pentene (28.3 g, 115 mmoles) prepared as in step B above, N-bromosuccinimide (20.4 g, 115 mmoles), carbontetrachloride (300 mL), and a few mgs of benzoyl peroxide is heated under strong reflux (325 W lamp) during 7.5 hours. After cooling and filtration, the solution is washed with water (100 mL, 3 times), dried over magnesium sulfate and concentrated. The oily residue (quantitative), consisting mainly of the title compound plus some 1-fluoro-2-phthalimido-4-methyl-5-bromo-3-pentene, is used for the next step without further purification.

(D) 1-Fluoro-2,5-diphthalimido-4-methylene-pentane and 1-fluoro-2,5-diphthalimido-4-methyl-3-(E,Z)-pentenes

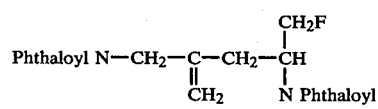

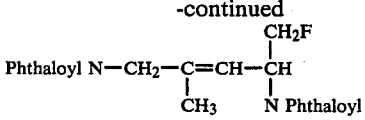

A mixture of 1-fluoro-2-phthalimido-4-methylene-5-bromo pentane (and isomers) (112 g, 345 mmoles) prepared as in step C above and potassium phthalimide (64 g, 345 mmoles) is heated at 80° C. in dry N, N-dimethylformamide (DMF) (200 mL) for 5 hours. After removal of the DMF under vacuum the colored residue is dissolved in chloroform and the organic solution is successively washed with water, twice with 1 N potassium hydroxide, once with 1 N hydrochloric acid and finally twice with brine. The organic solution is dried, discolored by filtration through two layers of silica gel and charcoal, and concentrated. The yellow oil obtained (110 g) is crystallized from ether/petroleum ether to give a mixture of isomers containing mainly 1-fluoro-2,5-diphthalimido-4-methylene-penetane together with some 1-fluoro-2,5-diphthalimido-4-methyl-3pentene (49 g). The mother liquors (59.7 g) chromatographed on silica gel (1 kg, ethyl acetate/petroleum ether 3/7) give 1-fluoro-2,5-diphthalimido-4-methyl-3-(Z)-pentene (4 g; 2 g after crystallization from ether), a mixture of the three title compounds (6 g) and pure 1-fluoro-2,5-diphthalimido-4-methylene-pentane (13 g). Overall yield of the three isomers: 50 %.

NMR data: 1-Fluoro-2,5-diphthalimido-4-methylene-pentane: NMR (CDCl₃): 2.67 (2H, m), 3.93-5.67 (3H, complex m), 4.23 (2H, broad s), 4.93 (2H, broad s), 7.70 (8H, m). 1-Fluoro-2,5-d iphthalimido-4-methyl-3-(Z)-pentene: NMR (CDCl₃): 1.70 (3H, broad s), 4.45 (2H, AB, $J_{AB}=8$ Hz), 4.10-5.73 (3H, complex m), 5.85 (1H, m), 7.80 (8H, m).

1-Fluoro-2,5-diphthalimido-4-methyl-3-(E)-pentene (not obtained pure) NMR (CDCl₃): 1.83 (broad s, H₃C—C—), 5.80 (m, —C=C—H)

(E) 1-Fluoro-2,5-diamino-4-methylene-pentane, dihydrochloride and 1-fluoro-2,5-diamino-4-methyl-3-pentenes

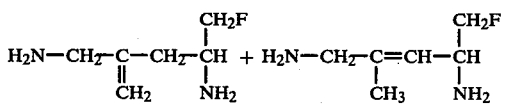

A mixture of 1-fluoro-2,5-diphthalimido-4-methylene pentane and isomers (3.93 g, 10 mmoles) obtained as in step D above and hydrazine hydrate (20 mL of a 1 molar solution in ethanol) is heated for 18 min at 90° C., and after addition of 15 mL of water and 25 mL of conc. hydrochloric acid, heated for an additional 5 min at the same temperature. After complete elimination of the excess of acid by evaporation, the residue is retreated under the same conditions as described above except that the heating with hydrazine hydrate is extended to 30 min. After dissolving the residue in water, removal of phthalhydrazide by filtration, and concentration under vacuum, the residue is dissolved in dry ethanol, and hydrazine dihydrochloride is removed by filtration. Evaporation gives a brownish oil which is used for the next step without further purification.

(F) 1-Fluoro,2,5-di-t-butoxycarbonylamino-4-methylenepentane and 1-Fluoro-2,5-di-t-butoxycarbonylamino-4-methyl-3-(E)-pentene The oil obtained as in Step E above (10 mmoles), di-t-butyl dicarbonate (5.23 g, 24 mmoles), triethylamine (3.03 g, 30 mmoles), water (6 mL), and tetrahydrofuran (30 mL) are kept at room temperature for 5 hours. After concentration and work-up with chloroform and water, 4.5 g of a colorless oil are obtained which is chromatographed on silica gel (ethyl acetate/petroleum ether: 2/8) to give 1-fluoro-2,5-di-t-butoxy-carbonylamino-4-methylene-pentane (1.7 g, 1.34 g after crystallization from ether/petroleum ether at $-4°$ C.) followed by mixed fractions and 1-fluoro-2,5-di-t-butoxy-carbonylamino-4methyl-3-(E)-pentene (1.08 g, 660 mg after crystallization from ether/petroleum ether). Overall yield for the 2 isomers (the cis-pentene derivative is assumed to have been lost during the hydrazine hydrate treatment) is nearly quantitative.

1-Fluoro-2,5-di-tert. butoxycarbonylamino-4-methylene-pentane.

NMR (CDCl$_3$): 1.38(18H, s), 2.25 (2H,d,J=7Hz), 3.67(2H,d,J=6Hz), 4.00(1H, broad m),
4.37(2H, d of m, J$_{H-F}$=47Hz), 4.90 (2H,2—NH—,m), 4.93(2H,m).

1-Fluoro-2,5-di-tert. butoxycarbonylamino-4-methylene-3-(E)-pentene.

NMR (CDCl$_3$): 1.43(18H,s), 1.73(3H, broad s), 3.65 (2H,d,J=7Hz), 4.35 (2H, d of m, J$_{H-F}$=48Hz), between 4.0 and 5.0 (3H, 2—NH—, broad m), 5.32(1H,m).

(G) 1-Fluoro-2,5-diamino-4-methyl-3-(E)-pentene, dihydrochloride

1-Fluoro-2,5-di-t-butoxycarbonylamino-4-methyl-3-(E)-pentene (650 mg, 1.96 mmole) obtained as in step F above is dissolved in dry ether saturated with hydrogen chloride gas. After standing overnight at room temperature, the white solid obtained by decantation is recrystallized from methanol/ether (320 mg, 80%).

NMR (D$_2$O/DCl): 1.85 (3H, broad s), 3.62 (2H, narrow m), 4.53 (1H, broad m), 4.62 (2H, d of m, J$_{H-F}$=46 Hz), 5.52 (1H, m) Anal. Calcd for C$_6$H$_{13}$N$_2$F.2HCl: C, 35.14; H, 7.37; N, 13.66 Found: C, 35.25; H, 7.13; N, 13.66

(H) 1-fluoro-2,5-diamino-4-methylene-pentane, dihydrochloride

1-Fluoro-2,5-di-t-butoxycarbonylamino-4-methylene-pentane (650 mg, 1.95 mmole) obtained was in S tep F above is dissolved in dry ether saturated with HCl gas. After standing overnight at room termperature, the while solid obtained is recrystallized from methanol/ether (350 mg, 87%).

NMR (D$_2$O,DCl): 2.75 (2H, d, J=8 Hz), 3.68 (2H, broad s), 3.97 (1H, broad m), 4.72 (2H, d of m, J$_{HF}$=48 Hz), 5.42 (2H, broad s) Anal. Calcd for C$_6$H$_{13}$N$_2$F.2HCl: C, 35.14; H, 7.37; N, 13.66 Found: C, 35.15; H, 7.14; N, 13.69

EXAMPLE 11

1-FLUORO-2,5-DIAMINO-3-METHYL-3-(E)-PENTENE,

DIHYDROCHLORIDE

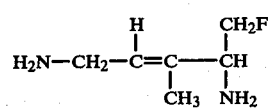

(A) Preparation of:
2-BROMO-4-ETHOXY-2-BUTENE

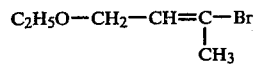

A freshly prepared solution of sodium ethoxide in dry ethanol (6.9 g Na, 0.3 mole, 100 ml EtOH) is added under nitrogen to 2,4-dibromo-2-butene (59 g, 0.275 mole) in 20 ml of dry ethanol. After 1.5 hours at room temperature, 100 ml of water is added to the reaction mixture, the product is extracted twice with small portions of petroleum ether and dried over magnesium sulfate. Distillation affords 2-bromo-4-ethoxy-2-butene.

(B) Preparation of:
1-FLUORO-2-AMINO-3-METHYL-5-ETHOXY-3-PENTENE

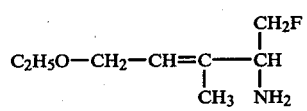

Under an atmosphere of nitrogen, 4-ethoxy-2-butene-2-yl-magnesium bromide is prepared from 8.25 g of 2-bromo-4-ethoxy-2-butene (50 mmoles) prepared as in Step A above, 12.15 g of magnesium turnings (500 mmoles) and 50 ml of dry tetrahydrofuran. After 4 hours the Grignard solution is transferred into another flask via a syringe, cooled to $-30°$ C. and fluoroacetonitrille (2.36 g, 40 mmoles) in tetrahydrofuran (30 ml) is added dropwise during 15 mins. After 15 additional minutes at $-30°$ C., a solution/suspension of sodium borohydride (1.52 g, 40 mmoles) in methanol (100 ml) and water (2ml) cooled to $-50°$ C. is poured into the reaction mixture previously cooled to $-50°$ C. The temperature rises up to $-30°$ C., and after stirring for 20 mins. at $-20°$ C., the mixture is allowed to warm up to $0°$ C. during 1 hour. After acidifying with 6N hydrochloric acid and evaporation, the residue is extracted twice with diethyl ether to remove by-products, made alkaline with 4N sodium hydroxide and extracted twice with diethyl ether. Evaporation of the solvent affords crude 1-fluoro-2-amino-3-methyl-5-ethoxy-3-pentene.

(C) Preparation of:
N-1-FLUORO-3-METHYL-5-ETHOXY-3-PENTENE-2-YL,
N$^1$-ETHOXYCARBONYL-o-PHTHALAMIDE

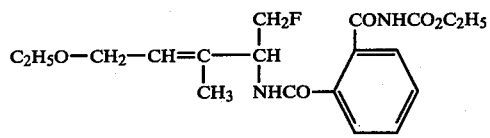

A mixture of 1-fluoro-2-amino-3-methyl-5-ethoxy-3-propene (1 g, 6.8 mmoles) prepared as in Step B above, N-ethoxycarbonylphthalimide (1.49 g, 6.8 mmoles) and 25 ml of dry benzene is kept over night at room temperature. The N-1-fluoro-3-methyl-5-ethoxy-3-pentene-2-yl, N$^1$-ethoxycarbonyl-o-phthalamide as isolated by evaporation of the solvent and is used for the following Step D, without purification.

(D) Preparation of:
1-FLUORO-2-PHTHALIMIDO-3-METHYL-5-ETHOXY-3-PENTENE

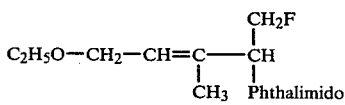

Treatment of N-1-fluoro-3-methyl-5-ethoxy-3-pentene-2-yl,N'-ethoxycarbonyl-o-phthalamide prepared as in Step C above with triethylamine (687 mg, 6.8 mmoles) in methylene chloride for 5 hours at room temperature followed by 2 extractions with 1 N hydrochloride acid and evaporation gives crude 1-fluoro-2-phthalimido-3-methyl-5-ethoxy-3-pentene.

Rapid chromatography on silica (ethyl acetate: petroleum either 15:85) gives three fractions: fraction A (150 mg), a mixed fraction B (385 mg) and fraction C (320 mg), A and C representing respectively pure cis-1-fluoro-2-phthalimido-3methyl-5-ethoxy-3-pentene and trans-1-fluoro-2phthalimido-3-methyl-5-ethoxy-3-pentene.

(E) Preparation of:
1-FLUORO-2-PHTHALIMIDO-3-METHYL-5-BROMO-3-(E)-PENTENE

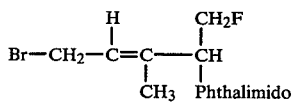

Boron tribromide (106 mg, 0.42 mmoles) in 5 ml of dry methylene chloride is added slowly to a solution of 1-fluoro-2-phthalimido-3-methyl-5-ethoxy-3-(E)-propene (i.e. trans), (336 mg, 1.15 mmoles) prepared as in Step D above in 10 ml of dry methylene chloride cooled at −78° C. The temperature is allowed to rise to room temperature overnight, the solvent is evaporated, and 1-fluoro-2-phthalimido-3-methyl-5-bromo-3-(E)pentene is obtained.

(F) Preparation of:
1-FLUORO-2,5-DIPHTHALIMIDO-3-METHYL-3-(E)-PENTENE

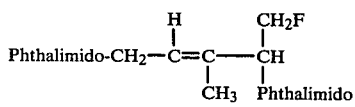

A mixture of 1-fluoro-2-phthalimido-3-methyl-5-bromo-3-(E)-pentene (360 mg, 1.10 mmole) prepared as in Step E above and potassium phthalimide (245 mg, 1.32 mmole) is heated at 80° C. in dry N,N-dimethylformamide (5 ml) for 2.5 hours. After cooling, water is added to the reaction mixture and the solid is filtered off. Chloroform 1 N potassium hydroxide extraction to remove the excess of phthalimide, drying, filtration and evaporation of the solvent afford 1-fluoro-2,5-diphthalimido-3-methyl-3-(E)-pentene.

(G) Preparation of:
1-FLUORO-2,5-DIAMINO-3-METHYL-3-(E)-PENTENE

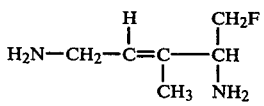

1-Fluoro-2,5-diphthalimido-3-methyl-3-(E)-pentene (10.5 g; 27.7 mmoles) prepared as in Step F above is heated at 95° C. in concentrated hydrochloric acid (250 ml) and acetic acid (100 ml) during 24 hours. After evaporation of the solvent, the residue is taken up in water and phthalic acid is filtered off. The filtrate is evaporated and the solid residue is crystallized from methanol-acetone to give 1-fluoro-2,5-diamino-3-methyl-3-(E)-pentene, dihydrochloride (4.2 g; 79%).

The dihydrochloride salt is dissolved in methanol, sodium methoxide (2 equivalents) added and the solution evaporated to dryness under reduced pressure. The residue is dissolved in absolute ethanol, filtered and the filtrate evaporated to dryness under reduced pressure to yield 1-fluoro-2,5-diamino-3-methyl-3-(E)pentene.

The following Examples relating to pharmaceutical compositions, the term "active compound" is used to indicate the compound 1-fluoro-2,5-diamino-4-methyl-3-(E)-pentene. This compound may be replaced in these compositions by any other compound of the invention, for example by 1-fluoromethyl-2,5-diamino-3-methyl-3-(E)-pentene. Adjustments in the amount of medicament may be necessary or desirable depending upon the degree of activity of the medicament as is well known in the art.

EXAMPLE III

An illustrative composition for hard gelatin capsules is as follows:

| (a) active compound | 20 mg |
| (b) talc | 5 mg |
| (c) lactose | 90 mg |

The formulation is prepared by passing the dry powders of (a) and (b) through a fine mesh screen and mixing them well. The powder is then filled into hard gelatine capsules at a net fill of 115 mg per capsule.

EXAMPLE IV

An illustrative composition for tablets is as follows:

| (a) active compound | 20 mg |
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE V

An illustrative composition for an injectable suspension is the following 1 ml ampul for an intramuscular injection:

| | weight percent |
|---|---|
| (a) active compound | 1.0 |
| (b) polyvinylpyrrolidone | 0.5 |
| (c) lecithin | 0.25 |
| (d) water for injection to make | 100.0 |

The materials (a)-(d) are mixed, homogenized, and filled into 1 ml ampuls which are sealed and autoclaved 20 minutes at 121° C. Each ampul contains 10 mg per ml of novel compound (a).

EXAMPLE VI

|  | mg/suppository |
|---|---|
| Active Compound | 50 |
| Oil of Theobroma | 950 |

The medicament is powdered and passed through a B.S. No. 100 sieve and triturated with molten oil of Theobroma at 45° C. to form a smooth suspension. The mixture is well stirred and poured into moulds each of nominal 1 G capacity, to produce suppositories.

EXAMPLE VII

The ODC inhibitory activity of the compounds of Formula I can be demonstrated in vivo according to the following procedure:

Male rats of the Sprague-Dawley strain (200–220 g body weight), purchased from Charles River, are given food and water ad libitum under a constant 12 hr light-12 hr dark lighting schedule. Drugs are injected intraperitoneally (dissolved in 0.9% saline) or are given by gavage (dissolved in water). Rats given saline or water serve as control. Five to six hours after drug administration, the animals are killed by decapitation and the ventral prostate, testis and thymus are excised rapidly and immediately processed. The tissues are homogenized with three volumes of 30 mM sodium phosphate buffer (pH 7.1) containing 0.1 mM EDTA, 0.25 M sucrose, 0.1 mM pyridoxal phosphate and 5 mM dithiothreitol. Ornithine decarboxylase activities are determined on a 1,000 g supernatant of testis or prostate homogenate and on a whole thymus homogenate, essentially as described by Ono et al (Biochem. Biophys. Acta, 284, 285 (1972)).

When tested according to the above-described procedure, the compound of Example I gave the results shown below at a single oral dose of 25 mg/kg body weight and 6 hours after administration.

| ODC ACITIVITY (% CONTROL) | | |
|---|---|---|
| VENTRAL PROSTATE | THYMUS | TESTIS |
| 36 | 46 | 53 |

EXAMPLE XII

The activity of the compounds of Formula I as inhibitors of ornithine decarboxylase (ODC) can be demonstrated in vitro according to the following procedure:

Ornithine decarboxylase (ODC) is prepared from the livers of rats which have been injected with thioacetamide (150 mg/kg of body weight) 18 hrs before sacrifice, and is purified about ten fold by acid treatment at pH 4.6 as described by Ono et al (Biochem. Biophys. Acta 284, 285 (1972)). The stock solution of ODC is comprised of protein (16 mg/mL), sodium phosphate buffer (30 mM, pH 7.1), dithiothreitol 5 mM) and pyridoxal phosphate (0.1 mM). The specific activity of this stock solution is 0.12 nmol of $CO_2$/min per mg of protein. For a typical experiment 320 $\mu$l of this stock solution are mixed at time 0 with 80 $\mu$l of a solution of the inhibitor in water and incubated at 37°. At different times 50 $\mu$l aliquots are transferred into a 1-mL assay medium containing sodium phosphate (30 mM, pH 7.1), dithiothreitol (5 mM), pyridoxal phosphate (0.1 mM), L-ornithine (0.081 $\mu$mol), and DL-[1-$^{14}$C] ornithine (0.043 $\mu$mol, 58 Ci/mol, Amersham) in a closed vessel in which a filter paper moistered with 50 $\mu$l hyamine hydroxide (1 M) is fitted. The reaction is allowed to proceed for 60 min at 37° C. and then terminated by addition of 0.5 ml of 40% trichloroacetic acid. After an additional 30 min the $CO_2$ absorbed on the filter paper is counted in a standard scintillation cocktail. $K_I$ (apparent dissociation constant) and $\tau_{50}$ (half-life, at infinite concentration of inhibitor are calculated according to the method of Kitz and Wilson (J. Biol. Chem., 237, 3245 (1962)).

When tested according to the above-described procedure, the compound of Example I gave the results shown in below. Half-life ($t_{\frac{1}{2}}$) at 10 $\mu$M is also set forth

TABLE III

| | ODC | |
|---|---|---|
| $K_I$ ($\mu$M) | $\tau_{50}$ (Min.) | $t_{\frac{1}{2}}$ (Min.) |
| 8.5 | 4.5 | 7.8 |

We claim:

1. A fluorinated alkenylene diamine derivative of the following Formula I:

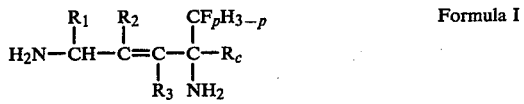

Formula I wherein:
$R_c$ represents hydrogen or $-COR_5$, where $R_5$ is as defined below;
$R_1$ represents hydrogen or $C_1$-$C_6$ alkyl;
one of $R_2$ and $R_3$ represents hydrogen and the other represents $C_1$-$C_6$ alkyl;
$R_5$ represents hydroxy or $C_1$-$C_8$ alkoxy; and
p represents 1 or 2
or a pharmaceutically acceptable salt thereof.

2. A compound as defined in claim 1 and having the following Formula IA:

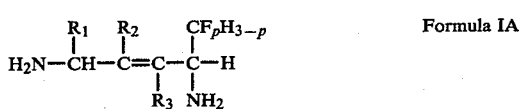

Formula IA wherein
$R_1$, $R_2$, $R_3$, and p are as defined in claim 1;
or a pharmaceutically acceptable salt thereof.

3. A compound as defined in claim 1 and having the following Formula IB:

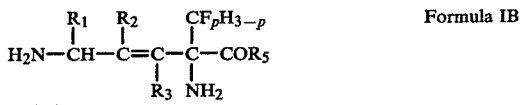

Formula IB wherein
$R_1$, $R_2$, $R_3$, $R_5$, and p are as defined in claim 1;
or a pharmaceutically acceptable salt thereof.

4. A compound as defined in claim 1 wherein $R_2$ represents $C_1$-$C_6$ alkyl and $R_3$ represents hydrogen.

5. A compound as defined in claim 4 wherein $R_2$ represents methyl.

6. A compound as defined in claim 1 wherein $R_3$ represents $C_1$–$C_6$ alkyl and $R_2$ represents hydrogen.

7. A compound as defined in claim 6 wherein $R_3$ represents methyl.

8. A compound as defined in claim 1 wherein $R_1$ represents hydrogen.

9. A compound as defined in claim 8 wherein $R_3$ represent hydrogen.

10. A compound as defined in claim 1 wherein $R_c$ represents carboxy.

11. A compound as defined in claim 1 wherein $R_c$ represents $C_2$–$C_9$ alkoxycarbonyl.

12. A compound as defined in claim 1 wherein p is 1.

13. A compound as defined in claim 1 wherein p is 2.

14. The compound as defined in claim 6 which is 1-fluoro-2,5-diamino-3-methyl-3-(E)-pentene or a pharmaceutically acceptable salt thereof.

15. The compound as defined in claim 4 which is 1-fluoro-2,5-diamino-4-methyl-3-(E)-pentene or a pharmaceutically acceptable salt thereof.

16. A pharmaceutical composition for inhibiting arnithine decarboxylase comprising a compound as defined in claim 1 as an active ingredient and a pharmaceutically acceptable carrier or diluent.

17. A pharmaceutical composition as claimed in claim 16 in unit dosage form containing 10 mg to 300 mg of said compound per unit dose.

* * * * *

UNITED STATES PATENT AND TRADEMARK OFFICE
CERTIFICATE OF CORRECTION

PATENT NO. : 4,423,073

DATED : December 27, 1983

INVENTOR(S) : F. Gerhart, et al.

It is certified that error appears in the above-identified patent and that said Letters Patent are hereby corrected as shown below:

At column 1, lines 51-56, the patent reads

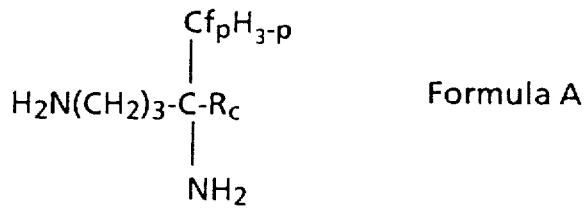

Formula A and should read

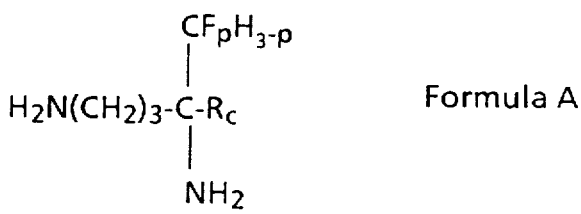

Formula A

At column 4, line 10, the patent reads 'salicyclic" and shoudl read --salicylic--

At column 4, line 63, the patent reads "4-methyl-3(E)-pentene;" and should read --4-methyl-3-(E)-pentene;--

At column 7, line 44, the patent reads "diethlether" and should read --diethylether--

At column 9, line 3, the patent reads "aluminumium" and should read --aluminum--.

UNITED STATES PATENT AND TRADEMARK OFFICE
CERTIFICATE OF CORRECTION

PATENT NO. : 4,423,073

DATED : December 27, 1983

INVENTOR(S) : F. Gerhart, et al.

It is certified that error appears in the above-identified patent and that said Letters Patent are hereby corrected as shown below:

At column 9, line 28, the patent reads "Formul III" and should read --Formula III- At column 11, line 61, the patent reads "steroisomers" and should read --stereoisomers--.

At column 12, line 32, the patent reads "accition" and should read --addition--

At column 13, line 6, the patent reads "hodroxide" and should read --hydroxide--

At column 15, lines 11 and 12, the patent reads "carbonylamino-4methyl-3-" and should read --carbonylamino-4-methyl-3- --

At column 15, line 45, the patent reads "obtained was in Step F" and should read --obtained as in Step F--

At column 16, line 62, the patent reads "-phthalamide as isolated by" and should read -- -phthalamide is isolated by--

At column 17, line 56, the patent reads "chloroform 1N potassium" and should read --chloroform/1N potassium--

UNITED STATES PATENT AND TRADEMARK OFFICE
CERTIFICATE OF CORRECTION

PATENT NO. : 4,423,073

DATED : December 27, 1983

INVENTOR(S) : F. Gerhart, et al.

It is certified that error appears in the above-identified patent and that said Letters Patent are hereby corrected as shown below:

At column 22, lines 7 and 8, the patent reads "arnithine" and should read --ornithine--

Signed and Sealed this

Thirty-first Day of May, 1988

Attest:

DONALD J. QUIGG

Attesting Officer

Commissioner of Patents and Trademarks